(12) United States Patent
Jin et al.

(10) Patent No.: US 11,150,230 B2
(45) Date of Patent: Oct. 19, 2021

(54) HYDROGEN SENSOR AND PREPARATION METHOD THEREFOR, AND METHOD FOR IMPLEMENTING HYDROGEN DETECTION

(71) Applicant: SUN YAT-SEN UNIVERSITY, Guangdong (CN)

(72) Inventors: Chongjun Jin, Guangdong (CN); Yang Shen, Guangzhou (CN); Xiaoyi She, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 0 days.

(21) Appl. No.: 16/496,803

(22) PCT Filed: Dec. 13, 2017

(86) PCT No.: PCT/CN2017/115825
§ 371 (c)(1),
(2) Date: Sep. 23, 2019

(87) PCT Pub. No.: WO2019/085165
PCT Pub. Date: May 9, 2019

(65) Prior Publication Data
US 2021/0102924 A1 Apr. 8, 2021

(30) Foreign Application Priority Data
Nov. 2, 2017 (CN) .......................... 201711064271.3

(51) Int. Cl.
*G01N 21/47* (2006.01)
*G01N 33/00* (2006.01)
(Continued)

(52) U.S. Cl.
CPC ........... *G01N 33/005* (2013.01); *G01N 21/47* (2013.01); *G01N 21/55* (2013.01); *G01N 21/59* (2013.01)

(58) Field of Classification Search
CPC ...... G01N 33/005; G01N 21/47; G01N 21/55; G01N 21/59; G01N 21/00; B81C 1/00
See application file for complete search history.

(56) References Cited

FOREIGN PATENT DOCUMENTS

| CN | 104807861 A | 7/2015 |
|---|---|---|
| CN | 205656120 U | 10/2016 |

(Continued)

OTHER PUBLICATIONS

Prabakaran Saravanan, "Self-lubricating SU-8 Nanocomposites for Microelectromechanical Systems Applications", Oct. 14, 2012, Springer (Year: 2012).*

(Continued)

*Primary Examiner* — Maurice C Smith
(74) *Attorney, Agent, or Firm* — Seyfarth Shaw LLP (57) ABSTRACT

A hydrogen sensor and preparation method therefor, and a method for implementing hydrogen detection using the hydrogen sensor. The hydrogen sensor comprises an elastic substrate and a hydrogen sensitive material-based nanofilm positioned on the elastomeric substrate. The preparation method for the hydrogen sensor comprises the following steps: mixing a liquid elastomeric material and a curing agent, and uniformly stirring the mixture to obtain a mixed liquid, wherein the mass ratio of the liquid elastomeric material to the curing agent is 5:1-20:1; removing bubbles in the mixed liquid; drying and curing the mixed liquid in which bubbles are removed to obtain an elastomeric substrate; and depositing a hydrogen sensitive nanomaterial on the elastomeric substrate to form a hydrogen sensitive material-based nanofilm. The hydrogen sensor and the method for implementing hydrogen detection using the hydrogen sensor feature high sensitivity and simple production.

7 Claims, 3 Drawing Sheets

(51) Int. Cl.
*G01N 21/55* (2014.01)
*G01N 21/59* (2006.01)

(56) References Cited

FOREIGN PATENT DOCUMENTS

| CN | 106959272 A | 7/2017 |
| CN | 107941787 A | 4/2018 |
| JP | 2005351754 A | 12/2005 |
| WO | 2019085166 A1 | 5/2019 |

OTHER PUBLICATIONS

Mustafa Eryurek "Optical sensor for hydrogen gas based on a palladium-coated polymer microresonator", Feb. 7, 2015, Elsevier (Year: 2015).*
Antonin Ollagniera, "Activation process of reversible Pd thin film hydrogen sensors", May 31, 2013, Elsevier (Year: 2013).*
International Search Report for Application No. PCT/CN2017/115825 dated Jul. 31, 2018, 2 pages.
Written Opinion for Application No. PCT/CN2017/115825 dated Jul. 31, 2018, 4 pages.
Search Report for Chinese Application No. 2017110642713 dated Apr. 24, 2019, 2 pages.
Office Action for Application No. 201711064271.3 dated Apr. 24, 2019, 6 pages.

\* cited by examiner

HYDROGEN SENSOR AND PREPARATION METHOD THEREFOR, AND METHOD FOR IMPLEMENTING HYDROGEN DETECTION

CROSS REFERENCE TO RELATED APPLICATIONS

This is a U.S. National Stage application of, and claims priority to, PCT/CN2017/115,825, filed Dec. 13, 2017, which further claims priority to Chinese Patent Application No. 2017110642713 filed Nov. 2, 2017, the disclosures of which are incorporated herein by reference in their entirety.

TECHNICAL FIELD

The present disclosure relates to a technical field of sensors, and more particularly, to a hydrogen sensor and a manufacturing method thereof, and a method of implementing hydrogen detection using the hydrogen sensor.

BACKGROUND

As a clean renewable energy carrier, hydrogen is considered as an ideal energy source to replace conventional fossil fuels. However, during the use of the hydrogen, the problem of security cannot be ignored. When a bulk density of the hydrogen is in a range of 4% to 75%, an explosion easily occurs. Therefore, a hydrogen sensor is very necessary for the application of the hydrogen.

The hydrogen sensor mainly includes sensors that senses with electricity and optical hydrogen sensor. Optical sensors mainly include surface plasmon sensors and sensors with film structure. The sensors with film structure are generally formed of multiple layers of metal or metallic compound nanofilm, and perform hydrogen measurement by using a change in dielectric constant generated by the nanofilm after absorbing the hydrogen. The change in hydrogen concentration may be determined by a change in reflectivity (transmittivity) intensity or by directly observing the color change on the surface of the sample.

Generally, the sensors with film structure mainly have a rigid substrate such as quartz plate or a silicon wafer on which a metal film is plated. The single layer film structure on the rigid substrate is less sensitive.

SUMMARY

Accordingly, as for the problem of how to improve the sensitivity of the hydrogen sensor, it is necessary to provide a hydrogen sensor and a manufacturing method thereof, and a method for implementing hydrogen measurement using the hydrogen sensor.

A hydrogen sensor includes an elastic substrate and a hydrogen sensitive material nanofilm positioned on the elastic substrate.

In one of the embodiments, the hydrogen sensitive material nanofilm is at least one selected from of the group consisting of palladium film, magnesium film, yttrium film, and nickel-magnesium alloy film.

In one of the embodiments, the hydrogen sensitive material nanofilm is palladium film, the hydrogen sensitive material nanofilm has a thickness of 5 nm to 420 nm.

In one of the embodiments, the hydrogen sensitive material nanofilm is selected from the group consisting of magnesium film, yttrium film, or nickel-magnesium alloy film, the hydrogen sensitive material nanofilm has a thickness of 5 nm to 800 nm.

In one of the embodiments, the hydrogen sensitive material nanofilm is a composite film composed of a palladium film and at least one other films selected from the group consisting of magnesium film, yttrium film and nickel-magnesium alloy film, the palladium film is positioned at the uppermost layer, wherein the palladium film has a thickness of 5 nm to 60 nm, and the other films have a thickness of 5 nm to 800 nm.

In one of the embodiments, a Young's modulus of the elastic substrate is greater than 0 and less than or equal to 60000 MPa.

In one of the embodiments, a surface of the elastic substrate adjacent to the hydrogen sensitive material nanofilm has a first patterned structure, the hydrogen sensitive material nanofilm has a second patterned structure matching the first patterned structure.

A method of manufacturing a hydrogen sensor as described above includes:

evaporating a hydrogen sensitive nanomaterial on an elastic substrate to form a hydrogen sensitive nanofilm.

In one of the embodiments, a manufacturing process of the elastic substrate includes the following steps:

mixing and stirring a liquid elastic material and a curing agent uniformly to form a mixed liquid, wherein the liquid elastic material and the curing agent have a mass ratio of 5:1 to 20:1;

removing bubbles in the mixed liquid; and drying and curing the mixed liquid after removing bubbles to obtain an elastic substrate.

A method for implementing hydrogen detection based on a hydrogen sensor as described above wherein includes:

irradiating an incident light onto a surface of the hydrogen sensitive material nanofilm, and measuring optical parameters of the hydrogen sensitive material nanofilm, wherein the optical parameters are a reflected light intensity, a reflectivity, a transmitted light intensity, a transmittivity, a scattered light intensity, a scattering cross-section, an extinction light intensity, an extinction cross-section, an absorbance or an absorption cross-section a gas containing hydrogen is introduced, the hydrogen sensitive material nanofilm expands in volume after absorbing hydrogen, and the elastic substrate deforms;

irradiating the incident light onto a surface of the deformed hydrogen sensitive material nanofilm, and measuring optical parameters of the deformed hydrogen sensitive material nanofilm; and obtaining a change in a relative optical parameter according to optical parameters of the hydrogen sensitive material nanofilm before and after deforming, and determining a concentration of hydrogen according to the change in the relative optical parameters.

According to the hydrogen sensor and the method for implementing hydrogen detection using the hydrogen sensor as described above, when the hydrogen sensitive material nanofilm is in contact with hydrogen, the hydrogen sensitive material nanofilm absorbs hydrogen, the hydrogen sensitive material expands in volume, and applies pressure to the surface of the elastic substrate during the expansion, causing the surface of the elastic substrate to deform and wrinkle, thereby causing the hydrogen sensitive material nanofilm to deform and wrinkle along with the elastic substrate. As an amount of hydrogen absorption gradually increases, the surface of the hydrogen sensitive material nanofilm gradually changes from a reflective surface to a scattering surface, thereby implementing a detection for hydrogen. The elastic substrate has elasticity, so that after the hydrogen sensitive material nanofilm absorbs hydrogen, the elastic substrate may response in time, it is advantageous to improving the sensitivity of the hydrogen sensor.

The aforementioned method of manufacturing the hydrogen sensor is not only simple in manufacture, low in cost, but also widely applicable.

DETAILED DESCRIPTION OF THE EMBODIMENTS

For the convenience of understanding the present disclosure, the present disclosure will be described more fully hereinafter with reference to the accompanying drawings. Preferred embodiments of the disclosure are shown in the drawings. The present disclosure may, however, be embodied in many different forms and are not be limited to the embodiments set forth herein. Rather, these embodiments are provided so that this disclosure will be understood thoroughly and completely.

Unless otherwise defined, all terms including technical and scientific terms used herein have the same meaning as commonly understood by one of ordinary skills in the art to which this disclosure belongs. The terms used in the description of the present disclosure is for the purpose of describing particular embodiments and is not intended to limit the present disclosure. The term "and/or" as used herein includes any and all combinations of one or more of the associated listed items.

Figure 1:
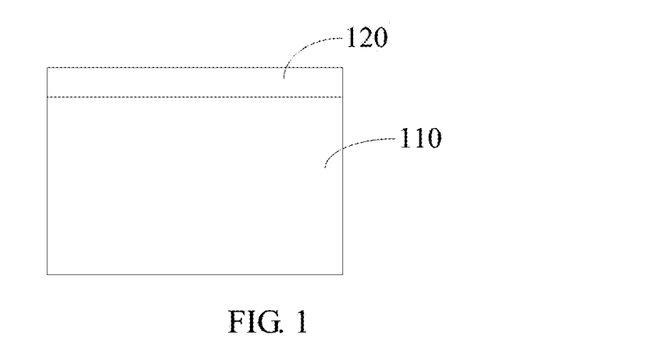
FIG. 1 is a schematic view of a hydrogen sensor according to an embodiment.

As shown in FIG. 1, a hydrogen sensor according to an embodiment includes an elastic substrate 110 and a hydrogen sensitive material nanofilm 120. The hydrogen sensitive material nanofilm 120 is positioned on the elastic substrate 110.

Figure 2:
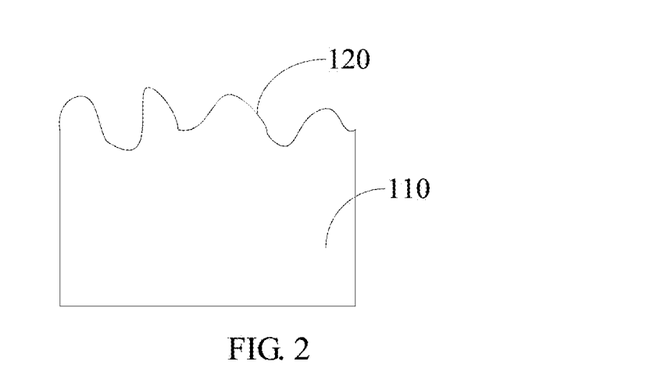
FIG. 2 is a schematic view of the hydrogen sensor of FIG. 1 after introducing hydrogen.

Therefore, when under a hydrogen atmosphere, the hydrogen sensitive material nanofilm 120 absorbs hydrogen, and the hydrogen sensitive material nanofilm 120 expands in volume. During the expanding process, the hydrogen sensitive material nanofilm 120 applies pressure to a surface of the elastic substrate 110, so that the surface of the elastic substrate 110 deforms and wrinkles, as shown in FIG. 2. Accordingly, the hydrogen sensitive material nanofilm 120 deforms and wrinkles along with the elastic substrate 110. As the amount of hydrogen absorbed by the hydrogen sensitive material nanofilm 120 gradually increases, the surface of the hydrogen sensitive material nanofilm 120 gradually changes from a reflective surface to a scattering surface, thereby implementing a detection for hydrogen. The elastic substrate 110 has elasticity, and thus after the hydrogen sensitive material nanofilm 120 absorbs hydrogen, the elastic substrate 110 may response in time, thereby improving the sensitivity of the hydrogen sensor. After dehydrogenating the hydrogen sensitive material nanofilm 120, due to the elastic restoring force of the elastic substrate 110, the elastic substrate 110 returns to the initial smooth state, causing the hydrogen sensitive material nanofilm 120 to return to a smooth state, and thus the hydrogen sensor returns to a smooth state, so that the hydrogen sensor may be used many times.

During the reaction of the hydrogen sensitive material nanofilm 120 with hydrogen, the detecting light irradiated on the surface of the hydrogen sensitive material nanofilm 120 changes from the reflected light to the scattered light, and thus a change in the received light intensity is obtained by the hydrogen sensor. Compared to conventional hydrogen sensors, the hydrogen sensor uses the principle of light scattering to detect hydrogen.

Figure 3:
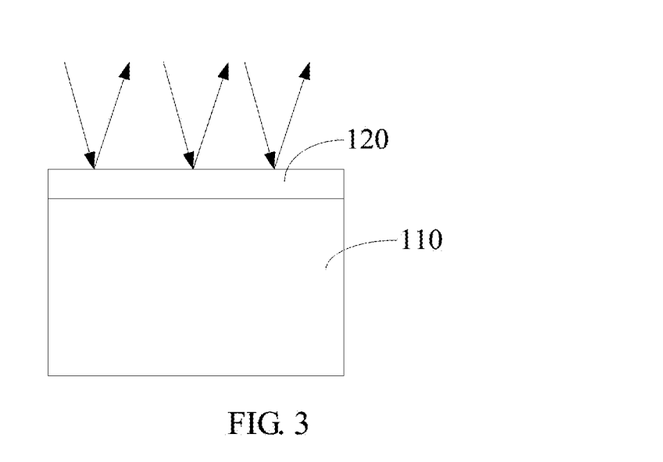
FIG. 3 is a schematic view showing an incident light irradiates the hydrogen sensor of FIG. 1.

Specifically, before introducing hydrogen, the detecting light irradiates on the surface of the hydrogen sensitive material nanofilm 120, and thus a reflection occurs, as shown in FIG. 3. The arrows in FIG. 3 indicate incidence and reflection. Accordingly, most of the reflected light is collected by the sensor.

Figure 4:
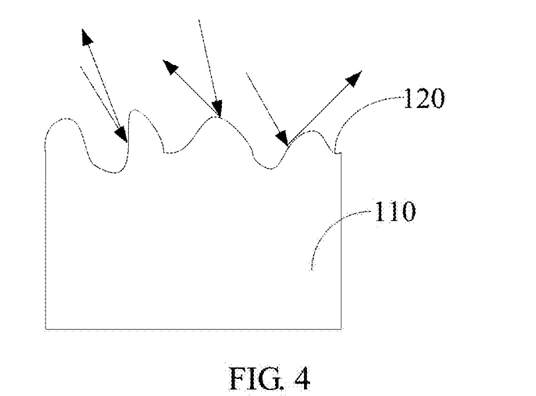
FIG. 4 is a schematic view showing an incident light irradiates the hydrogen sensor of FIG. 2.

After 4% hydrogen (a mixed gas of hydrogen and nitrogen, with a volume ratio of hydrogen to nitrogen of 4:96) is introduced, under the effect of the volume expansion of the hydrogen sensitive material nanofilm 120, the surface of the hydrogen sensor becomes rough. When the detecting light irradiates on the surface of the hydrogen sensitive material nanofilm 120, the light changes from the reflected light to the scattered light, as shown in FIG. 4. The arrows in FIG. 4 indicate incidence and scattering. As the propagation distance of the scattered light increases, the light intensity per unit area thereof decreases. Therefore, the light collected by the detector is greatly weakened.

In an embodiment, the hydrogen sensitive material nanofilm 120 is at least one selected from of the group consisting of palladium film, magnesium film, yttrium film, and nickel-magnesium alloy film. It should be noted that, the nanomaterial used in the hydrogen sensitive material nanofilm 120 may be other metal or metal composite that may expend in volume after absorbing hydrogen.

In one of the embodiments, the hydrogen sensitive material nanofilm 120 is palladium film having a thickness of 5 nm to 420 nm. The palladium film may react well with hydrogen at an environment of ambient temperature and pressure. The thickness of hydrogen sensitive material nanofilm 120 may affect the restoring state of the elastic substrate 110 after being dehydrogenated. Furthermore, in one of the embodiments, the hydrogen sensitive material nanofilm 120 has a thickness of 14 nm to 85 nm.

In another embodiment, the hydrogen sensitive material nanofilm 120 may be magnesium film, an yttrium film, or a nickel-magnesium alloy film. When the hydrogen sensitive material nanofilm 120 is a magnesium film, an yttrium film, or a nickel-magnesium alloy film, the hydrogen sensitive material nanofilm 120 may have a thickness of 5 nm to 800 nm.

Since the magnesium film, the yttrium film, the nickel-magnesium alloy film or the like has a low hydrogen absorption efficiency at ambient temperature and pressure, the hydrogen sensitive material nanofilm 120 may be a composite film composed of a palladium film and at least one selected from the group consisting of magnesium film, yttrium film and nickel-magnesium alloy film. In the composite film, the palladium film is positioned at the uppermost layer, and the palladium film has a thickness of 5 nm to 60 nm, and other films have a thickness of 5 nm to 800 nm. By locating the palladium film at the uppermost layer, the palladium film functions as a catalyst, and thus the sensing property of the composite film is improved.

The composite film may be a composite film in which the magnesium film and the palladium film are sequentially laminated, a composite film in which the yttrium film and the palladium film are sequentially laminated or a composite film in which the nickel-magnesium alloy film and the palladium film are sequentially laminated. When the composite film is the composite film in which the magnesium film and the palladium film are sequentially laminated, the magnesium film in the composite film has a thickness of 5 nm to 800 nm, the palladium film has a thickness of 5 nm to 60 nm. When the composite film is the composite film in which the yttrium film and the palladium film are sequentially laminated, the yttrium film in the composite film has a thickness of 5 nm to 800 nm, the palladium film has a thickness of 5 nm to 60 nm. When the composite film is the composite film in which the nickel-magnesium alloy film and the palladium film are sequentially laminated, the nickel-magnesium alloy film in the composite film has a thickness of 5 nm to 800 nm, the palladium film has a thickness of 5 nm to 15 nm. It should be noted that the composite film may be a composite film in which a magnesium film, an yttrium film and a palladium film are sequentially laminated.

In one of the embodiments, a Young's modulus of the elastic substrate 110 is greater than 0 and less than or equal to 60000 MPa. The elastic substrate 110 may be any elastomer that has low elastic modulus. The elastic substrate 110 may be a thermoset elastomer and a thermoplastic elastomer. The thermoplastic elastomer may be a rubber such as styrene butadiene rubber, polybutadiene rubber, isoprene rubber, ethylene propylene rubber, butyl rubber, neoprene rubber, nitrile rubber or the like. The thermoplastic elastomer may also be a polyurethane-based thermoplastic elastomer, a polyamide-based thermoplastic elastomer, a polyolefin-based thermoplastic elastomer or the like. The thermoset elastomer may be polysiloxane, polyurethane, silicone rubber or the like. It should be noted that the elastic substrate 110 is only required to have elasticity. The polysiloxane may be polydimethylsiloxane.

In one of the embodiments, a surface of the elastic substrate 110 adjacent to the hydrogen sensitive material nanofilm 120 has a first patterned structure. In this case, the hydrogen sensitive material nanofilm 120 has a second patterned structure matching the first patterned structure. Furthermore, a characteristic linearity of the second patterned structure may be greater than a wavelength magnitude of the incident light, so that the second patterned structure exhibits characteristics of the film. The characteristic linearity of the second patterned structure refers to a length, widths and the like thereof. The wavelength magnitude of the incident light refers to the wavelength of the incident light. In addition, materials used in the second patterned structure may be palladium, magnesium, yttrium, and nickel-magnesium alloy. It should be noted that the first patterned structure may be a grid mesh structure. The first patterned structure may also be other patterns, which may be chosen according to actual needs.

The hydrogen sensor as described above detects the hydrogen concentration at low concentrations by measuring changes in reflection intensity of the hydrogen sensor. A change in the relative reflectivity intensity of the hydrogen sensor may exceed 800% over the entire visible light area, under the effect of 4% hydrogen concentration. Such a strong change in the relative reflectivity intensity may be directly observed by naked eyes. The sensor is low in cost, simple in manufacture, may be mass-produced, has high sensitivity and is widely applicable, and is suitable for hydrogen detection in different environments.

A method of manufacturing the hydrogen sensor as described above according to an embodiment includes the following steps: evaporating a hydrogen sensitive nanomaterial on an elastic substrate to form a hydrogen sensitive nanofilm.

Specifically, the elastic substrate is placed into a magnetron sputtering apparatus, the hydrogen sensitive nanomaterial is evaporated on the elastic substrate, and thus the hydrogen sensitive nanofilm is formed. The sputtering parameter may be 15 mA/240 s.

The hydrogen sensitive nanomaterial may be palladium, yttrium, magnesium, nickel-magnesium alloy or the like. Therefore, the formed hydrogen sensitive nanofilm may be a palladium film. The palladium film may have a thickness of 5 nm to 420 nm. The formed hydrogen sensitive nanofilm 120 may be a magnesium film, yttrium film, or nickel-magnesium alloy film.

When the hydrogen sensitive nanofilm is a single layer film of magnesium film, yttrium film, nickel-magnesium alloy film or the like, the magnesium film, yttrium film, or nickel-magnesium alloy film may have a thickness of 5 nm to 800 nm. Since the magnesium film, yttrium film or the like has a low hydrogen absorption efficiency at ambient temperature and pressure, the hydrogen sensitive material nanofilm 120 may be a composite film composed of a palladium film and at least one other films selected from the group consisting of magnesium film, yttrium film and nickel-magnesium alloy film. In the composite film, the palladium film is positioned at the uppermost layer. By further forming the palladium film on the magnesium film, the yttrium film or the like, the palladium film functions as a catalyst, and thus the sensing property of the composite film is improved. Therefore, the nanomaterial such as magnesium, the yttrium, the nickel-magnesium alloy or the like is evaporated on the elastic substrate to form the magnesium film, the yttrium film, the nickel-magnesium alloy film or the like, and then the palladium nanomaterial is evaporated on the magnesium film, the yttrium film, the nickel-magnesium alloy film or the like to form the palladium film.

In addition, the elastic substrate 110 may be any elastomer that has low elastic modulus. The elastic substrate 110 may be a thermoset elastomer and a thermoplastic elastomer. The thermoplastic elastomer may be a rubber such as styrene butadiene rubber, polybutadiene rubber, isoprene rubber, ethylene propylene rubber, butyl rubber, neoprene rubber, nitrile rubber or the like. The thermoplastic elastomer may also be a polyurethane-based thermoplastic elastomer, a polyamide-based thermoplastic elastomer, a polyolefin-based thermoplastic elastomer or the like. The thermoset elastomer may be polysiloxane, polyurethane, silicone rubber or the like. It should be noted that the elastic substrate 110 is only required to have elasticity. In present embodiment, the polysiloxane may be polydimethylsiloxane.

In one of the embodiments, a method of manufacturing the elastic substrate includes the following steps.

In step S1, a liquid elastic material and a curing agent are mixed and stirred uniformly to obtain a mixed liquid. Specifically, the liquid elastic material may be an elastomer such as polysiloxane, polyurethane, or the like. At room temperature, the liquid elastic material and the curing agent are mixed at a mass ratio of 5:1 to 10:1, and poured into a petri dish for mixing. Then, the liquid elastic material and the curing agent is stirred uniformly to obtain a mixed liquid. The curing agent may be a silicone curing agent. In the present embodiment, the elastic material may be is polydimethylsiloxane (model: SYLGARD 184; manufacturer: Dow Corning, USA), and the curing agent is silicone curing agent (model: SYLGARD 184; manufacturer: Dow Corning, USA).

In step S2, bubbles in the mixed liquid are removed.

A clean silicon wafer is taken to be placed in another petri dish, the mixed liquid in step S1 is poured into the petri dish in which the silicon wafer is placed. The petri dish is placed in a vacuum pump for vacuumizing, and the bubbles in the mixed liquid are removed.

In step S3, an elastic substrate is obtained by drying and curing the mixed liquid in which the bubbles are removed. The drying conditions may be: a temperature of 60° C. to 80° C. and a time of 1.5 hours to 2 hours.

Specifically, the mixed liquid in which the bubbles are removed in step S2 is placed into an oven, dried at 60° C. to 80° C. for 1.5 hours to 2.5 hours. The petri dish is taken out after curing. An elastic film having a size of 2 cm * 2 cm was cut with a clean knife as an elastic substrate. It should be noted that the size of the elastic film may be selected according to actual needs.

In another embodiment, the manufacture method of the elastic substrate includes the following steps. In step 1), template is fabricated. Specifically, a structure complementary to a first patterned structure is fabricated on a rigid substrate using electron beam, focused ion beam or dual beam exposure techniques. The rigid substrate may be glass, silicon wafer or the like. In step 2), the sample is copied. The liquid elastic material and the curing agent are mixed at a ratio and then are coated on the rigid substrate in step 1), and after vacuuming, heat curing is performed to form an elastic substrate, and the elastic substrate is peeled off from the rigid substrate. Thus, the first patterned structure is formed on the surface of the elastic substrate. In step 3), a hydrogen sensitive metal is evaporated on the elastic substrate obtained in step 2) to form a second patterned structure. The second patterned structure is complementary to the first patterned structure. The hydrogen sensitive metal may be palladium, magnesium, yttrium, nickel-magnesium alloy or the like.

A method for implementing hydrogen detection based on the hydrogen sensor according to an embodiment includes the following steps.

In step S10, an incident light is irradiated onto a surface of the hydrogen sensitive material nanofilm, and an optical parameter of the hydrogen sensitive material nanofilm is measured. The optical parameter may be a reflected light intensity, a reflectivity, a transmitted light intensity, a transmittivity, a scattered light intensity, a scattering cross-section, an extinction light intensity, an extinction cross-section, an absorbance or an absorption cross-section. In the present embodiment, the optical parameter is the reflectivity. The reflectivity of the hydrogen sensitive material nanofilm may be measured by using an ultraviolet spectrophotometer.

In step S20, a gas containing hydrogen is introduced, the hydrogen sensitive material nanofilm expands in volume after absorbing hydrogen, and the elastic substrate deforms.

Specifically, the introduced hydrogen is a mixed gas of hydrogen and nitrogen. For example, 4% hydrogen is introduced, which refers to that a mixed gas of hydrogen and nitrogen (the volume ratio of hydrogen to nitrogen is 4:96) is introduced. The hydrogen sensitive material nanofilm expands in volume after absorbing hydrogen, and applies pressure to a surface of the elastic substrate during the expansion process, causing the surface of the elastic substrate to deform and wrinkle, so that the hydrogen sensitive material nanofilm deforms along with the elastic substrate.

In step S30, an incident light is irradiated onto a surface of the deformed hydrogen sensitive material nanofilm, and an optical parameter of the deformed hydrogen sensitive material nanofilm is measured. In the present embodiment, the optical parameter is a reflectivity. The reflectivity of the hydrogen sensitive material nanofilm may be measured by using an ultraviolet spectrophotometer.

In step S40, a change in the relative optical parameter is obtained through measuring optical parameters of the hydrogen sensitive material nanofilm before and after deformation, and a concentration of hydrogen is determined according to the change in the relative optical parameter.

Specifically, in the present embodiment, the change in the relative reflectivity intensity is calculated by measuring reflectivity before and after the deformation of the hydrogen sensitive material nanofilm. Then, the change in the relative reflectivity intensity is compared with a relationship information between the hydrogen concentrations and the changes in the relative reflectivity intensity, to determine the concentration of hydrogen being introduced. It should be noted that the relationship information between the hydrogen concentration and the change in the relative reflectivity intensity may be a lookup table or the like, the lookup table represents the changes in relative reflectivity intensity corresponding to different hydrogen concentrations.

It should be noted that when the optical parameter is the scattered light intensity, the scattered light intensity of the scattered light before and after introducing hydrogen in any direction other than the reflected direction is measured. Therefore, the concentration of the hydrogen is determined according to the change in the scattered light intensity.

The present disclosure will be further set forth below through specific embodiments.

EXAMPLE 1

(1) At a room temperature, a polydimethylsiloxane and a curing agent were mixed at a mass ratio of 5:1 and poured into a petri dish for mixing. Then, the polydimethylsiloxane and the curing agent was stirred uniformly to form a mixed liquid.

(2) A clean silicon wafer was taken and placed in another petri dish, the mixed liquid was poured into the petri dish in which the silicon wafer was placed. The petri dish was placed in a vacuum pump for vacuumizing, and the bubbles in the mixed liquid were removed.

(3) The mixed liquid in which the bubbles were removed was placed into an oven, dried at 70° C. for 2 hours. The petri dish was taken out after curing. A polydimethylsiloxane film having a size of 2 cm * 2 cm was cut with a clean knife as an elastic substrate.

(4) A surface of the polydimethylsiloxane film being in contact with the silicon wafer was regarded as a substrate surface, and the polydimethylsiloxane film was placed into a magnetron sputtering apparatus, the palladium nanomaterials was evaporated on the substrate surface to obtain a palladium nanofilm. The palladium nanofilm had a thickness of 34 nm, the sputtering parameter was 15 mA/240 s.

The hydrogen sensor manufactured in Example 1 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 674%.

EXAMPLE 2

The hydrogen sensor was manufactured according to the steps of Example 1, except that a polydimethylsiloxane and a curing agent were mixed at a mass ratio of 10:1.

The hydrogen sensor manufactured in Example 2 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 887%.

EXAMPLE 3

The hydrogen sensor was manufactured according to the steps of Example 1, except that a polydimethylsiloxane and a curing agent were mixed at a mass ratio of 20:1.

The hydrogen sensor manufactured in Example 3 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 353%.

EXAMPLE 4

The hydrogen sensor was manufactured according to the steps of Example 2, except that the palladium nanofilm had a thickness of 5 nm.

The hydrogen sensor manufactured in Example 4 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 8%.

EXAMPLE 5

The hydrogen sensor was manufactured according to the steps of Example 1, except that the palladium nanofilm had a thickness of 14 nm.

The hydrogen sensor manufactured in Example 5 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 196%.

EXAMPLE 6

The hydrogen sensor was manufactured according to the steps of Example 1, except that the palladium nanofilm had a thickness of 85 nm.

The hydrogen sensor manufactured in Example 6 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 2970%.

EXAMPLE 7

The hydrogen sensor was manufactured according to the steps of Example 1, except that the palladium nanofilm had a thickness of 420 nm.

The hydrogen sensor manufactured in Example 7 was placed into a gas flow cell, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet spectrophotometer (Lambda 950, PerkinElmer). At a wavelength of 500 nm, the change in the relative reflectivity was measured to be 1968%.

Figure 5:
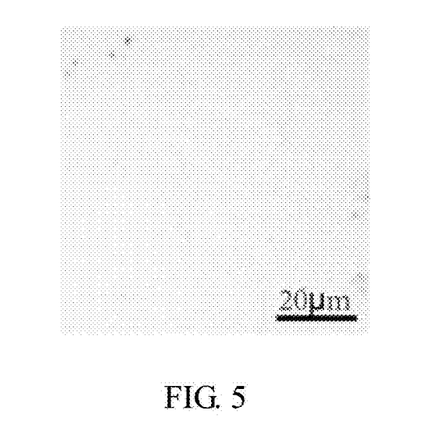
FIG. 5 is a microscope photograph of the hydrogen sensor of FIG. 1.

Observing the change in surface of the hydrogen sensor before and after introducing hydrogen The hydrogen sensor manufactured in Example 2 was placed under a microscope before introducing hydrogen, and observed with a 10× objective lens. The microscope was connected to an image sensor, and thus the picture shown in the objective lens was transmitted to a display through the image sensor. The observation result observed on the display was shown in FIG. 5. It is shown that the surface of the hydrogen sensor was relatively smooth, the intensity of the reflected light was large.

Figure 6:
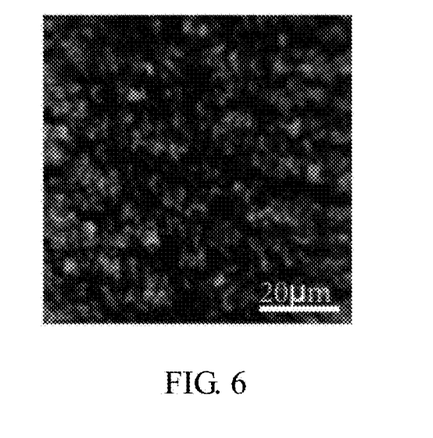
FIG. 6 is a microscope photograph of the hydrogen sensor of FIG. 2.

The hydrogen sensor manufactured in Example 2 was placed under a microscope after introducing 4% hydrogen, and observed with a 10× objective lens. The microscope was connected to an image sensor, and thus the picture shown in the objective lens was transmitted to a display through the image sensor. The observation result observed on the display was shown in FIG. 6. It can be clearly observed that the surface of the hydrogen sensor was wrinkled and rapidly darkened, and the reflected light intensity was getting lower and lower.

Spectral Measurement

The hydrogen sensor was placed into a gas flow cell, and the reflectance spectrum of the hydrogen sensor was measured by using an ultraviolet spectrophotometer (Lambda 950, PerkinElmer). The detector was 32 cm away from the hydrogen sensor, the size of the light collection area was 7 mm * 7 mm. First, a silver mirror was placed in the gas flow cell to measure the reflectivity of the silver mirror. Using the reflectivity of the silver mirror in the flow cell, the glass lens in the gas flow cell was calibrated for errors in the detected light reflection. The calibration formula is $$R = \frac{R_S - R_B}{R_{Ag} - R_B},$$

where Rs is the reflectivity of the hydrogen sensor, $R_{Ag}$ is the reflectivity of the silver mirror, and $R_B$ is the reflectivity of the background.

Figure 7:
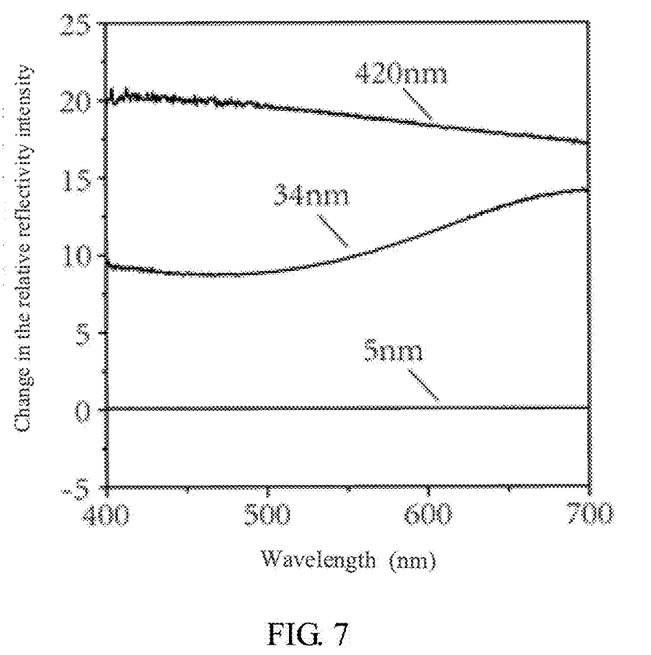
FIG. 7 is a graph showing the relative reflectivity change of the hydrogen sensor having palladium films with different thicknesses.

As shown in FIG. 7, the thickness of the palladium film was different, the change in the relative reflectivity was different. It can be seen from the drawings, when the thickness of the palladium film was 85 nm, the relative intensity of the reflectivity spectrum changed the most, and the sensing effect was the best. The calculation formula of the change in the relative reflectivity is: $\Delta R_{rel}=(R_0\%-R_i\%)/R_i\%$, i is greater than 0 and less than or equal to 4, $\Delta R_{rel}$ is the change in the relative reflectivity, $R_0\%$ is the reflectivity before introducing hydrogen, $R_i\%$ is the reflectivity of hydrogen with a concentration of i % being introduced.

When the thickness of the palladium film was 34 nm, while the hydrogen with a concentration of 4% was introduced, the reflectivity decreases by 40% or more and the relative reflectivity intensity changes by 800% in the entire visible light region, compared with the reflectivity measured before introducing hydrogen.

Figure 8:
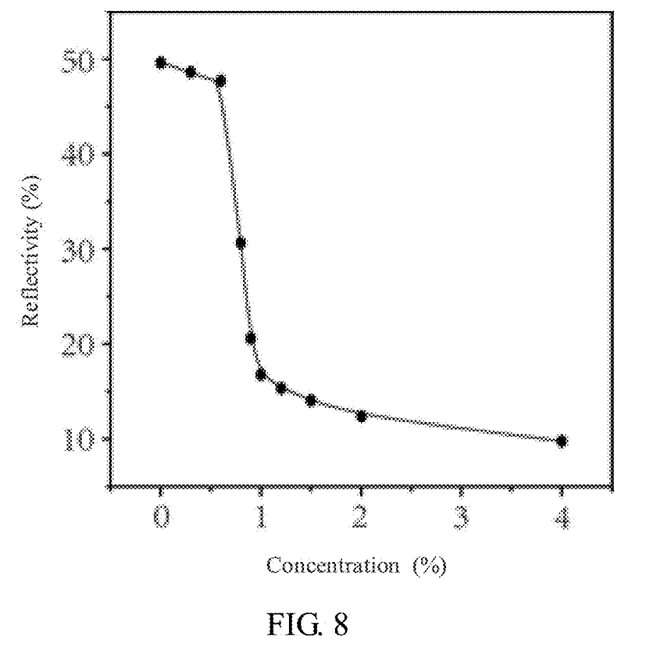
FIG. 8 is a relational graph showing the reflectivity of the hydrogen sensor at different hydrogen concentrations.

Referring again to FIG. 8, FIG. 8 shows the spectral response at different hydrogen concentrations. The reflection spectrum of the hydrogen sensor under different concentrations of hydrogen was measured under probe light having a wavelength of 500 nm. The concentrations of the hydrogen were 0%, 0.3%, 0.6%, 0.8%, 0.9%, 1%, 1.2%, 1.5%, 2% and 4%, respectively. It can be seen from FIG. 8, the linear measuring range of the hydrogen sensor was between 0.6% and 1% of the hydrogen concentration, and it can be seen that the hydrogen sensor had a higher sensitivity.

The technical features of the above-described embodiments may be combined arbitrarily. To simplify the description, not all the possible combinations of the technical features in the above embodiments are described. However, all of the combinations of these technical features should be considered as being within the scope of the present disclosure, as long as there are no contradictions in such combinations.

The above embodiments only represent several embodiments of the present disclosure, and the description thereof is relatively specific and detailed, but they should not be construed as limiting the scope of the present disclosure. It should be noted that, for those skilled in the art, several variations and improvements may be made without departing from the concept of the present disclosure, and these belong to the protection scope of the present disclosure. Therefore, the protection scope of the present disclosure shall be defined by the appended claims.

What is claimed is:

1. A hydrogen sensor, comprising:
   an elastic substrate having a Young's modulus greater than 0 and less than or equal to 60,000 MPa; and
   a hydrogen sensitive material nanofilm positioned on the elastic substrate,
   wherein a surface of the elastic substrate adjacent to the hydrogen sensitive material nanofilm has a first patterned structure, and
   wherein the hydrogen sensitive material nanofilm has a second patterned structure matching the first patterned structure.

2. The hydrogen sensor according to claim 1, wherein the hydrogen sensitive material nanofilm is at least one selected from a group consisting of palladium film, magnesium film, yttrium film, and nickel-magnesium alloy film.

3. The hydrogen sensor according to claim 2, wherein the hydrogen sensitive material nanofilm is palladium film, and the hydrogen sensitive material nanofilm has a thickness of 5 nm to 420 nm.

4. The hydrogen sensor according to claim 1, wherein the hydrogen sensitive material nanofilm is selected from a group consisting of magnesium film, yttrium film, and nickel-magnesium alloy film, and wherein the hydrogen sensitive material nanofilm has a thickness of 5 nm to 800 nm.

5. The hydrogen sensor according to claim 2, wherein the hydrogen sensitive material nanofilm is a composite film composed of palladium film and at least one other film selected from a group consisting of magnesium film, yttrium film and nickel-magnesium alloy film, wherein the palladium film is positioned at an uppermost layer, and wherein the palladium film has a thickness of 5 nm to 60 nm, and the other film has a thickness of 5 nm to 800 nm.

6. A method of manufacturing a hydrogen sensor, comprising:
   mixing and stirring a liquid elastic material and a curing agent uniformly to form a mixed liquid, wherein the liquid elastic material and the curing agent have a mass ratio of 5:1 to 20:1;
   removing bubbles in the mixed liquid;
   drying and curing the mixed liquid, after removing bubbles, to obtain an elastic substrate; and
   evaporating a hydrogen sensitive nanomaterial on the elastic substrate to form a hydrogen sensitive nanofilm.

7. A method for implementing hydrogen detection based on a hydrogen sensor, comprising:
   irradiating an incident light onto a surface of a hydrogen sensitive material nanofilm;
   measuring optical parameters of the hydrogen sensitive material nanofilm, wherein the optical parameters are a reflected light intensity, a reflectivity, a transmitted light intensity, a transmittivity, a scattered light intensity, a scattering cross-section, an extinction light intensity, an extinction cross-section, an absorbance or an absorption cross-section;
   introducing a gas containing hydrogen;
   expanding the hydrogen sensitive material nanofilm in volume after absorbing hydrogen;
   deforming an elastic substrate and a hydrogen sensitive material nanofilm;
   irradiating the incident light onto a surface of the deformed hydrogen sensitive material nanofilm;
   measuring optical parameters of the deformed hydrogen sensitive material nanofilm; and
   obtaining a change in a relative optical parameter according to optical parameters of the hydrogen sensitive material nanofilm before and after the step of deforming; and
   determining a concentration of hydrogen according to the change in the relative optical parameter.

* * * * *